United States Patent [19]

Bamford et al.

[11] 4,345,036

[45] Aug. 17, 1982

[54] OPTICAL GLASS FIBRES AND METHOD OF FORMING SUCH FIBRES

[75] Inventors: Charles R. Bamford, Southport; James R. Mellor, Ormskirk; Bernard Parker, Billinge Nr. Wigan, all of England

[73] Assignee: Pilkington Brothers Limited, Merseyside, England

[21] Appl. No.: 225,818

[22] Filed: Jan. 16, 1981

[30] Foreign Application Priority Data

Jan. 28, 1980 [GB] United Kingdom ............... 8002834

[51] Int. Cl.³ .................... C03B 37/075; C03C 1/10; C03C 3/02; C03C 3/04
[52] U.S. Cl. ........................ 501/37; 65/3.15; 65/31; 350/96.34; 501/54; 501/64
[58] Field of Search ............... 65/3.15, 13, 31; 501/37, 64, 54; 350/96.34

[56] References Cited

U.S. PATENT DOCUMENTS

| | | | |
|---|---|---|---|
| 2,219,332 | 10/1940 | Pirani | 501/64 X |
| 2,958,604 | 11/1960 | George | 501/54 |
| 3,499,775 | 3/1970 | Albinak et al. | 501/64 |
| 3,528,829 | 9/1970 | Baak et al. | 501/64 X |
| 4,110,093 | 8/1978 | Macedo et al. | 65/31 X |

FOREIGN PATENT DOCUMENTS 816412  7/1959 United Kingdom .
1527436 10/1978 United Kingdom .

OTHER PUBLICATIONS

Evans et al., "Radiation Resistant Fiber Optic Materials . . .", IEEE Transactions on Nuclear Science, Dec. 1975, vol. NS-22, No. 6, pp. 2462–2467.
Kaiser, "Drawing-Induced Coloration in Vitreous Silica Fibers", J. Am. Optical Soc., Apr. 1974, vol. 64, No. 4, pp. 475–481.

Primary Examiner—Richard V. Fisher
Attorney, Agent, or Firm—Sughrue, Mion, Zinn, Macpeak & Seas

[57] ABSTRACT

In optical glass fibres formed of high-silica glass which is susceptible to the production of color centers on drawing into fibres, the attenuation due to such drawing-induced color centers is suppressed or reduced by incorporating from 1 to 100 (preferably 3 to 50) parts per million of cerium oxide in the glass from which the fibre is drawn, under oxidizing conditions such that a significant proportion of the cerium is in the form of ceric ions and the total attenuation is not more than 20 dB/Km in the wavelength range from 800 to 900 nm. The invention is applicable to the known process in which a batch of glass-forming materials is melted to form a phase-separable silicate glass and a rod is drawn or cast from the glass, which is then phase-separated and leached to form a porous rod; the rod is stuffed with a dopant which increases the refractive index; the dopant is dissolved out from an outer region of the rod, which is collapsed by heating to produce a pre-form of a high silica glass with an inner region of higher refractive index; and optical fibre is drawn from the pre-form. In this process, a cerium compound may be introduced into the batch, the melting and the drawing or casting of the rod then being carried out under oxidizing conditions, or a cerium compound may be introduced with the dopant into the porous rod.

12 Claims, 3 Drawing Figures

OPTICAL GLASS FIBRES AND METHOD OF FORMING SUCH FIBRES

BACKGROUND OF THE INVENTION

1. Field of the Invention

This invention relates to optical glass fibres and to methods of forming such fibres.

2. Description of the Prior Art

Optical fibres for use in communication systems are required to have a low level of absorption or attenuation of light signals transmitted through them, so as to keep to a minimum the number of signal repeaters required in a transmission line. By careful control of the manufacturing process, so as to eliminate impurities, it is possible to reduce the attenuation to a figure of 10 dB per kilometer or less, but it is then found that attenuation due to colour centres induced in the fibre while it is being drawn can become important with certain types of high-silica optical glass fibre. The formation of such colour centres when drawing fibres from vitreous silica was reported by P. Kaiser in J. Am. Optical Soc., 64, 475 (1974). The principal wavelength of the absorption band caused by the colour centres was 630 nm. Optical fibres are generally drawn from pre-forms, i.e. glass rods with an outer region or cladding of lower refractive index than the inner region or core. In drawing fibres from pre-forms which have been made of a high-silica glass composition by the method disclosed in U.K. Patent No. 1,527,436, in which the core glass is modified by the addition of an alkali metal oxide which increases its refractive index, we have found a marked optical absorption band in the fibres centred at a wavelength of 510 nm, which is not found in optical attenuation measurements on the pre-forms and which disappears when the fibres are heated to about 500° C. This absorption maximum at 510 nm can be as high as 250 dB/Km and the absorption band can be of such width that the attenuation in the range of wavelengths normally used in communication systems employing optical fibres, namely 800 to 900 nm, can be up to 20 dB/Km.

On the other hand, the high-silica glass compositions formed by the technique known as chemical vapour deposition and certain other high-silica glass compositions which are also used for drawing optical fibres and which employ additives such as $GeO_2$ and $P_2O_5$ to raise the refractive index of the core glass, do not appear to suffer from drawing-induced colour centre formation.

Colour centre formation in glasses is known to occur also as a result of the action of ionising radiation on the glass and cerium oxide in amounts of 1 to 2% by weight has been incorporated in glasses used, for example, for face plates in cathode ray tubes in order to suppress the formation of radiation-induced colour centres.

It has further been suggested by B. D. Evans and G. H. Sigal, Jnr., in IEEE Transactions on Nuclear Science, Vol. NS-22, No. 6, December 1975, pages 2462 to 2467, that it should be possible to reduce the sensitivity of optical fibres to ionising radiation and to improve the speed of recovery of light transmission by such fibres on removal of the radiation, by using fibres of silicate-based glasses incorporating cerium, though the known cerium-doped silicate glass fibres referred to in their paper, incorporating 0.2% to 1.2% Ce, were shown to have fairly high intrinsic losses (attenuations). In the operating wavelength range of 800 to 900 nm, we have found that the attenuation due to incorporation of cerium at these levels exceeds the attenuation due to drawing-induced colour centres which would be found in the absence of cerium.

U.K. Patent No. 816,412 describes the use of a smaller proportion of cerium, in a mean proportion of less than $10^{-3}$, in a glass otherwise consisting of pure silica, in order that the glass should retain its initial transparency in the visible spectrum and be free of induced radioactivity after having been subjected to the action of electromagnetic radiations or elementary particles, the glass being intended, for example, for making ampoules for irradiated liquids, for transparent windows or for optical assemblies which are intended for examination of articles liable to emit electromagnetic radiations or elementary particles. This glass is said, however, to show an ultraviolet absorption band with a maximum at 3200 A (320 nm). For the purposes indicated in Specification No. 816,412, an overlap of this band into the visible spectrum would be unlikely to cause problems. In an optical fibre communication system, however, because the typical path length is a kilometer or more, the resulting attenuation could be significant.

SUMMARY OF THE INVENTION

The present invention is not primarily concerned with suppression of radiation-induced colour centres, but has the object of suppressing drawing-induced colour centres in fibres drawn from high-silica glasses which are susceptible thereto, i.e. those containing at least 85 mol % $SiO_2$ and particularly those which contain alkali metal oxide additives to raise the refractive index of the core glass, so as to enable the production of optical glass fibres with particularly low intrinsic attenuation levels.

According to the present invention, in a method of forming an optical fibre from a high-silica glass which contains at least 85 mol % $SiO_2$ and which is susceptible to the production of colour centres on drawing into fibres, attenuation due to such drawing-induced colour centres is suppressed or reduced by incorporating from 1 to 100 parts per million of cerium oxide in the glass from which the fibre is drawn, under oxidising conditions such that a significant proportion of the cerium in the glass of the fibre is in the form of ceric ions and the fibre has a total attenuation of not more than 20 dB/Km in the wavelength range from 800 to 900 nm. Preferably the amount of cerium oxide incorporated in the glass used to form the fibre and the conditions of incorporation, are such that the glass contains from 1 to 50 parts per million by weight of ceric ions.

We have found that by ensuring that a significant proportion of the cerium is in the ceric form, it is possible to suppress or reduce the formation of drawing-induced colour centres with a sufficiently small addition of cerium, namely 1 to 100 parts per million, to avoid introducing unacceptable attenuation due to the cerium itself, at the operating wavelengths. At this level of cerium addition, the fibre is still susceptible to radiation-induced colour centres though its rate of recovery therefrom is increased as compared with a cerium-free fibre otherwise of the same composition.

In the preferred case, the total amount of cerium incorporated in the glass used to form the fibre is from 3 to 50 parts per million.

A known method of making optical fibres, described in U.K. Patent No. 1,527,436, comprises the steps of melting a batch of glass-forming materials to form a phase-separable silicate glass and drawing or casting a rod of the glass; causing separation of silicate and non-silicate phases in the glass rod; leaching out the non-silicate phase to leave a porous rod; stuffing the porous rod with a dopant which increases the refractive index of the glass; dissolving the dopant out from an outer region of the porous rod; collapsing the porous rod by heating to produce a pre-form of a high-silica glass with an inner region of higher refractive index; and drawing an optical fibre from the pre-form. This method is particularly suited to the practice of the present invention, by adopting a course wherein a cerium compound is introduced into the glass before the step of collapsing the porous rod, the operating conditions being such that in the pre-form and in the fibre a significant proportion of the cerium, amounting to 1 to 50 parts per million by weight of the glass, is in the form of ceric ions.

In one embodiment of the invention, using this method, the cerium compound is introduced into the batch and the melting and the drawing or casting of the rod are carried out under oxidising conditions to ensure that a significant proportion of the cerium in the glass rod is in the form of ceric ions. The leaching of the porous rod removes a large proportion of the cerium from the glass, but leaves a small quantity in the pre-form, so the quantity of cerium in the batch should be substantially greater than the required quantity in the fibre. For example, the cerium compound may be introduced into the batch so that the phase-separable silicate glass contains from 0.1% to 1% by weight $CeO_2$ and preferably from 0.1% to 0.5% $CeO_2$. Such quantities are more easily controlled and thus render it easier to ensure the required small quantities in the fibre.

In an alternative embodiment, still using the same general method, the cerium compound is introduced with the dopant into the porous rod and the porous rod is collapsed under oxidising conditions to ensure that a significant proportion of the cerium is in the form of ceric ions. In this embodiment, the cerium compound may be a cerous salt which is oxidised during the collapsing of the rod to produce the ceric ions and in a preferred case the dopant is caesium nitrate and the cerium compound is cerous nitrate, both being applied to the porous rod in the same aqueous solution. The desired small quantity of cerium can thus be introduced into the porous rod in an easily controlled manner and converted into ceric form in the pre-form.

The invention also resides in an optical glass fibre drawn from a glass containing at least 85 mol % silica and from 1 to 50 parts per million by weight of ceric ions, the attenuation characteristics of the fibre being such that the curve of attenuation plotted against wavelength shows no peaks due to drawing-induced colour centres and the attenuation in the wavelength range from 800 to 900 nm is not more than 20 dB/Km. Preferably the total cerium in the fibre (cerous ions and ceric ions) is from 3 to 50 parts per million by weight of the glass.

It is believed that the present invention can be employed with advantage, by incorporating a level of cerium below that which is likely to cause a greater problem in increasing attenuation rather than reducing it by suppression of drawing-induced colour centres, in any high silica glass where the fibres drawn from pre-forms of that glass are found otherwise to have an absorption peak due to colour centre formation. The ceric ions cause suppression or reduction to an acceptable level of the attenuation arising at the operating wavelength. We believe that, in those glasses which are susceptible to drawing induced colour centre formation, the defect formation mechanism may be associated with the presence of certain dopants or additives used to raise the refractive index of the core glass, such as alkali metal oxides and, in particular, caesium oxide. The invention is thus applicable to the drawing of optical fibres from high silica glasses which include, in addition to those made by the methods disclosed in U.K. Pat. No. 1,527,436, glasses which are at least 85 mol % silica but contain alkali metal oxide additions of the order of 5 to 15 mol % by weight or more to raise the refractive index.

We have found that measurement of levels of the total cerium in the fibres at the quantities used, i.e. normally below 50 ppm, is difficult but we have found that quantities apparently as low as 4 ppm cerium can have an effect in wholly or partially suppressing the absorption band due to drawing-induced colour centres.

The amount of cerium oxides in a glass is normally expressed in a chemical analysis as cerium dioxide, but as the active material in the present case is the ceric ion, figures are given for cerium. Some cerous ion will be present in most cases, as it is difficult to convert it completely to the ceric state. Measurement of the ratio of ceric ions to cerous ions is also difficult and prone to error particularly at very low levels. The ratio of ceric to cerous ion in the fibre depends on the effective oxygen partial pressures applied during the manufacture of the pre-form and during drawing of the fibre. The effectiveness of very small quantities of cerium in suppressing absorption due to drawing-induced colour centres indicates that the cerium in the fibre is wholly or substantially wholly in the form of ceric ions. Analysis indicates that a level of 1 to 50 ppm ceric ion is adequate to suppress or reduce the absorption peak due to drawing-induced colour centres.

In the case where the cerium is incorporated in the glass batch used to form the phase-separable silicate glass (generally a borosilicate glass) from which are drawn or cast the rods which are converted by phase separation, leaching, stuffing and collapsing to the pre-forms from which the optical fibres are drawn, with cerium dioxide levels in the batch of up to 1% by weight, a few ppm of cerium is always left in the finished pre-form, even though most of the cerium is removed by the phase separation and leaching stages. The concentration of cerium in the pre-forms is typically less than one hundredth of the quantity of cerium in the initial borosilicate glass. In general, satisfactory results can be obtained by adding from 0.1% to 0.5% $CeO_2$ to the batch. Amounts in excess of 0.5% $CeO_2$ can be used and acceptable results have been obtained with up to 1% $CeO_2$ except that one must take care not to employ so much $CeO_2$ that melting problems are encountered nor to retain so much cerium in the final fibre that the attenuation rises to above 30 dB/Km in the wavelength range from 800 to 900 nm.

We find it satisfactory to use about 0.5% cerium dioxide as at this level the glass can be refined to the very high standards necessary and the fully processed pre-forms contain an adequate concentration of ceric ions.

It is essential that the glass be melted under oxidising conditions so as to ensure that cerium is present with a significant proportion in the ceric state in the glass. This means that refining agents should be so chosen as to avoid any reducing effect on cerium in the melt. We have found that if, for example, $As_2O_3$, which has a reducing action on cerium, is added as a refining agent, there is no suppression of the absorption peak present in the absorption curve due to colour centre formation during drawing, because the cerium is present predominantly as cerous ion.

Comparative analyses of glasses, one melted under reducing conditions with 0.8% $As_2O_3$ present and the other under oxidising conditions, gave the following approximate distribution of ceric and cerous ions:

| Conditions | % $Ce^{3+}$ | % $Ce^{4+}$ |
|---|---|---|
| Reducing: $As_2O_3$ present | 100 | 0 |
| Oxidising | 75 | 25 |

These results confirm that under reducing conditions a glass is formed with the cerium present predominantly in the cerous state. Under oxidising conditions, the proportion of ceric ions in the rods can be around 25%, but in the fibre the proportion is generally much higher, as indicated above.

If one follows the alternative course mentioned above, of incorporating the cerium compound with the dopant into the porous rod and collapsing the porous rod under oxidising conditions, a soluble cerium salt or salts will normally be added to the dopant or dopants which are incorporated in the porous rods to provide a refractive index modification in the solid glass pre-form. If the dopant is, for example, added as a solution of caesium nitrate, then cerous nitrate would be added to the dopant solution because it is not possible to add a ceric salt, as we have found that the only stable soluble ceric salts are double salts such as ceric ammonium nitrate which are not stable in the presence of a dopant such as caesium nitrate. It has been found that the addition of a cerium salt which is soluble in the dopant solution used and the use of severe oxidising conditions during the collapsing stage will ensure that the fibre, when drawn from the pre-form, contains sufficient of the cerium in the ceric state to suppress any peaks in the attenuation curve which would normally occur due to the presence of drawing-induced colour centres. It is important to ensure that the total quantity of cerium used in the dopant solution does not cause the drawn fibre to have an unacceptable attenuation, either as a result of absorption by excess of cerium (over 100 ppm) or due to light scattering from particles of $CeO_2$ which have been unable to be fully dissolved even during fibre drawing. We find that, for example, the addition of 10 to 15 gm cerous nitrate to 1500 ml of aqueous solution containing 1500 gm caesium nitrate gives an effective concentration of 1 to 20 ppm cerium in the ceric state in the drawn fibre. It is difficult to lay down limits as the quantities needed will vary to some extent with the nature of the dopant solution being used. For example, the concentration of the caesium nitrate solution will vary according to the refractive index modification required and this in turn will affect the required concentration of cerous nitrate.

DETAILED DESCRIPTION

EXAMPLE 1

Figure 1:
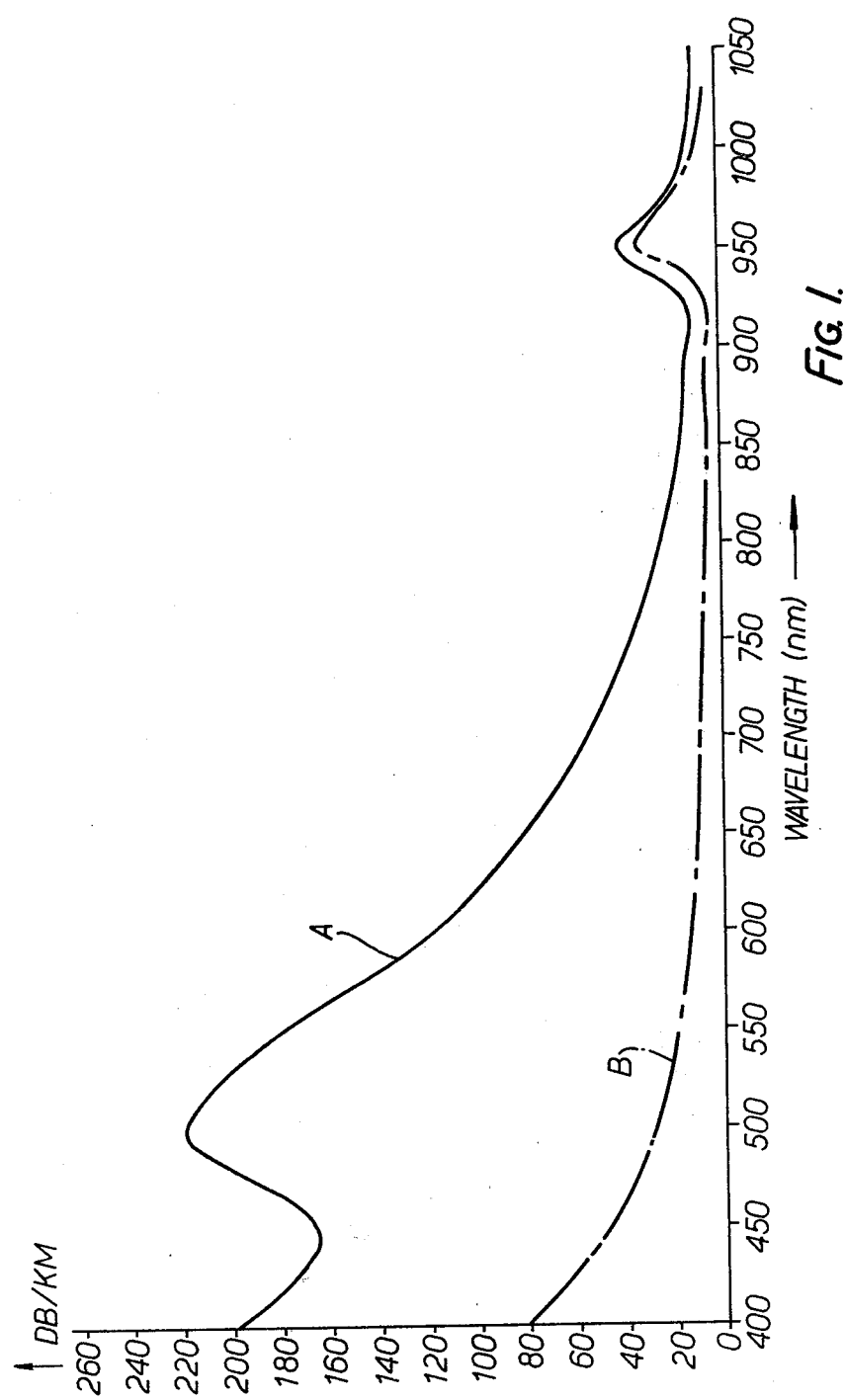
FIG. 1 is a graphical representation of the attenuation plotted against wavelength for light transmitted through an optical fibre in accordance with the invention, compared with an otherwise similar fibre not containing cerium.

In order to determine the effect on the attenuation of the finished fibre of adding cerium to the batch in a manner to cause production of a significant proportion of ceric ions, a series of melts of a phase-separable borosilicate glass having a basic composition in mol %:

| | |
|---|---|
| $SiO_2$ | 56% |
| $B_2O_3$ | 36% |
| $K_2O$ | 4% |
| $Na_2O$ | 4% | were carried out under oxidising conditions. The cerium was added to the batch in the form of ceric ammonium nitrate and the quantity added was varied from that required to give 0.1 wt% to 1.0 wt% $CeO_2$ in the borosilicate glass rods cast from the melt. The rods were then converted into pre-forms suitable for drawing optical fibres by the method disclosed in British Patent No. 1,527,436, i.e. causing phase separation, leaching out the non-silicate phase, stuffing the porous rod with a dopant (caesium oxide) which increases the refractive index, dissolving the dopant out of an outer region of the porous rod and collapsing the porous rod by heating to obtain the pre-form.

The specific procedure followed was that the cast rods, having a diameter of 10 mm, were heat treated at 550° C. for 2 hours to cause phase separation, after which each rod was etched for 10 seconds in 5% HF followed by a 30-second wash in water.

The rods were leached at 95° C. with 3 N HCl containing 20% $NH_4Cl$ by weight for in excess of 30 hours, to leach out the borate phase.

The leached material was washed with de-ionized water. The rods were then doped in the following manner: Porous rods produced by the procedure outlined above were immersed for more than four hours at 95° C. in an aqueous solution of $CsNO_3$ with a concentration of 1500 g $CsNO_3$/1000 ml solution. An outer region of lower refractive index, i.e. an optical cladding, was generated by immersing the rods in water at 0° C. to dissolve out precipitated caesium nitrate from the pores in this outer region. The rods were then dried in vacuum at 0° C. and then consolidated into pre-forms by raising them to a temperature at which collapsing takes place (around 800° C.) under a pressure of oxygen (approximately 1/5th bar), so as to produce oxidising conditions for obtaining a significant proportion of ceric ions in the glass of the pre-forms.

The quantity of cerium in the pre-forms was measured as cerium using a part of each pre-form. Fibre was drawn from the remainder of the pre-form and the spectral attenuation measured over the wavelength range from 400 to 1050 nm.

The analytical data both on the initial borosilicate rod and on the fibre pre-form and the associated fibre spectral attenuation date, are summarised in Table I.

TABLE I

| Rod No. | % CeO$_2$ in Borosilicate glass | Cerium in preform ppm | Attenuation of fiber in dB/Km at wavelengths specified in nm | | | | |
|---|---|---|---|---|---|---|---|
| | | | 500 | 600 | 700 | 800 | 900 |
| 1 | 0.3 | 8 | 33 | 19 | 14 | 11 | 9 |
| 2 | 0.5 | 4 | 32 | 16 | 11 | 8 | 7 |
| 3 | 0.5 | 5 | 31 | 15 | 10 | 7 | 6 |
| 4 | 0.5 | 8 | 32 | 18 | 11 | 8 | 6 |
| 5 | 0.5 | 12 | 27 | 13 | 8 | 6 | 6 |
| 6 | 0.75 | 19 | 31 | 17 | 15 | 16 | 12 |

A typical spectral attenuation curve for fibres containing cerium is shown in FIG. 1, curve B. The degree of change achieved by the addition of cerium is illustrated by a comparison of curve B with curve A, corresponding to a pre-form not containing cerium. However, a significant proportion of the cerium must be in the ceric state, as indicated above. If the cerium is predominantly in the cerous state, as occurs when 0.8% arsenic oxide is added to the borosilicate glass with the cerium, then there is no suppression of the drawing-induced colour centre absorption.

EXAMPLE II

To demonstrate the results of adding cerium in the stuffing stage of the process, a series of porous rods were prepared as follows, using a similar procedure to that described in Example I. A glass having the same basic composition in mol % as that described in Example I was melted and stirred to produce a homogeneous melt from which rods were drawn having a diameter of 10 mm.

The drawn rods were heat treated at 550° C. for two hours to cause phase-separation and each rod was etched for 10 seconds in 5% HF followed by a 30 second wash in water. The rods were leached, washed and doped as in Example I, except that the CsNO$_3$ solution also contained cerous nitrate (Ce(NO$_3$)$_3$) in the amounts set out in Table II below. The generation of the cladding, drying and consolidation of the rods to produce the pre-forms again followed the procedure of Example I.

Fibre was then drawn from the consolidated pre-forms and the spectral attenuation in the wavelength range from 400 to 1050 nm measured. The total Ce concentration was also determined by chemical analysis. The attenuation was in all cases below 20 dB/Km in the range from 800 to 900 nm and the absorption peak had been substantially suppressed. Table II below summarises the spectral attenuation data and gives the Ce level in ppm in the case of the pre-forms.

TABLE II

| Rod No. | Weight of Cerous Nitrate (gms) | Cerium in preform ppm | Attenuation of fiber in dB/Km at wavelengths specified in nm | | | | |
|---|---|---|---|---|---|---|---|
| | | | 500 | 600 | 700 | 800 | 900 |
| 7 | 10 | 94 | 78 | 30 | 18 | 13 | 10 |
| 8 | 15 | 105 | — | — | 27 | 18 | 15 |
| 9 | 15 | 73 | — | 52 | 31 | 19 | 16 |

EXAMPLE III

The procedure used in Example I was repeated for a further series of rods using in all cases 0.5 weight % CeO$_2$ in the batch. The level of Ce in the core and cladding portions of the rod before drawing was measured and is given in Table III below. In all cases there was suppression of the absorption peak and band which would have been expected in the absence of ceric ions.

TABLE III

| Rod No. | Ce Level ppm | | Attenuation dB/Km at 900 nm |
|---|---|---|---|
| | Core | Cladding | |
| 10 | 4 | 6 | 8 |
| 11 | 13 | 5 | 12 |
| 12 | 16 | 7 | 6 |
| 13 | 12 | 5 | 6 |
| 14 | 12 | 27 | 12 |

Figure 2:
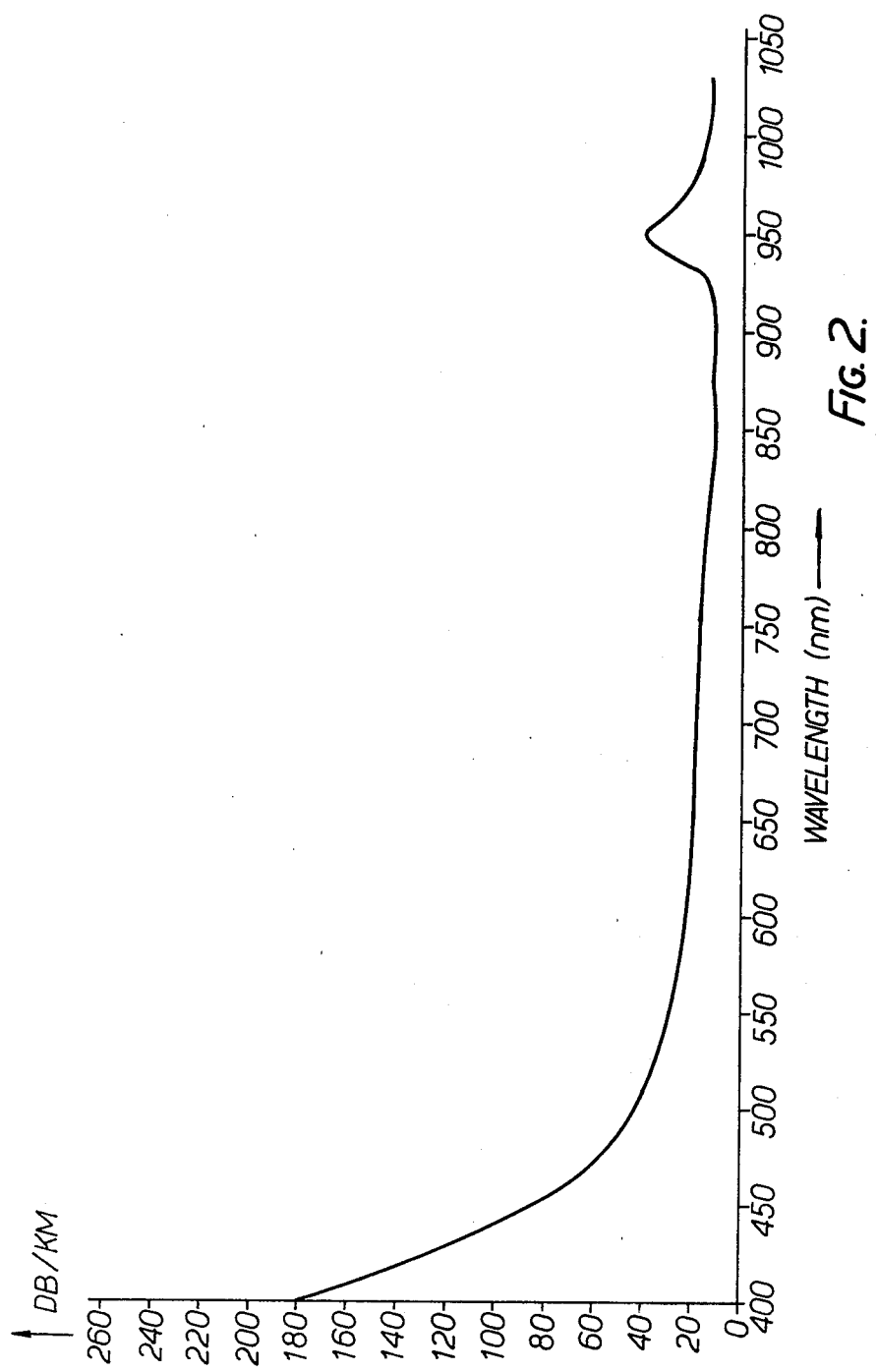
FIG. 2 shows a similar curve for another fibre according to the invention.

FIG. 2 illustrates the attenuation curve achieved.

Figure 3:
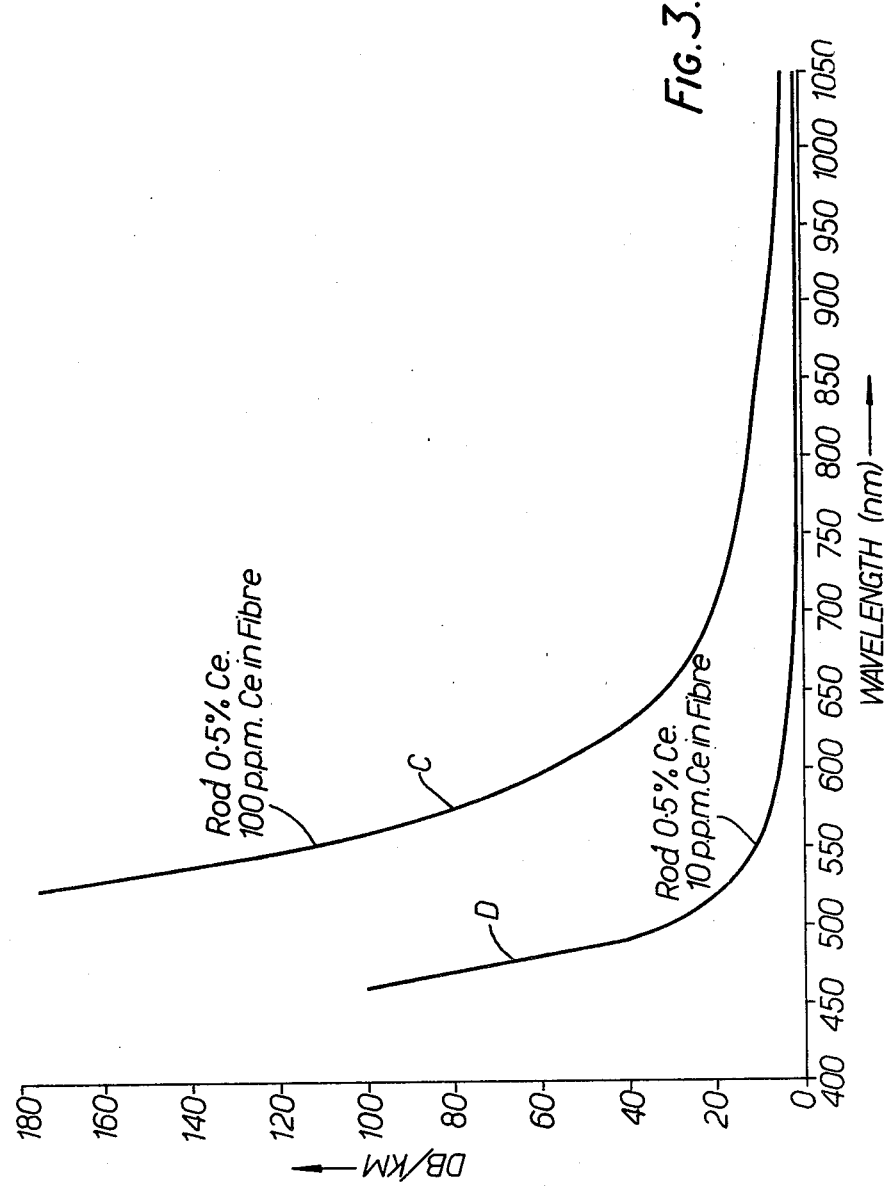
FIG. 3 is a similar representation of extrapolated curves for cerium-containing glasses before drawing into fibres.

To demonstrate the importance of keeping the total amount of the cerium in the fibre at a low level, a borosilicate rod 1 meter in length was made of the same basic composition as the phase-separable glass rods in the Examples above, with 0.5% CeO$_2$ in the rod and the attenuation produced in light transmitted through the rod was measured for a variety of wavelengths. Beer's Law states that the absorption of light by a glass, for a given thickness of the layer traversed, depends on the molecular concentration of the colourant in that layer. On this basis, the results of the measurements on the rod were expressed in dB/Km for 10 ppm and 100 ppm levels of cerium and are plotted in FIG. 3. The intrinsic attenuation caused by the cerium is shown by the curves in FIG. 3. With 100 ppm total cerium, as in curve C, the attenuation at 850 nm due to cerium is 10 dB/Km, showing that 100 ppm should be considered the maximum for total cerium content if the fibre is to have the desired low attenuation. With 10 ppm cerium (curve D) the attenuation due to cerium at 850 nm is only 1 dB/Km.

The composition of the fully processed pre-form and of the fibre drawn from it is of course quite different from that of the initial borosilicate glass rod. The pre-form consists of at least 85 mol % SiO$_2$. However, the spectral attenuation due to cerium, at least 50% of which is in the ceric state to prevent or reduce formation of colour centres during drawing of fibres, can be expected to be of the same order in the pre-form as in the borosilicate rod. Thus it is evident that quantities of cerium above 100 ppm must not be used.

Although the fibres of the invention are not intended to have decreased sensitivity to colour centre formation induced by ionising radiation, it has been found that they do recover from such effects of radiation considerably faster than similar fibres not containing cerium.

We claim:

1. A method of forming an optical fibre from a high-silica glass which contains at least 85 mol % SiO$_2$ and which is susceptible to the production of colour centres on drawing into fibres, wherein attenuation due to such drawing-induced colour centres is suppressed or reduced by incorporating from 1 to 100 parts per million of cerium oxide in the glass from which the fibre is drawn, under oxidising conditions such that a significant proportion of the cerium in the glass of the fibre is in the form of ceric ions and the fibre has a total attenuation of not more than 20 dB/Km in the wavelength range from 800 to 900 nm.

2. A method according to claim 1 wherein the amount of cerium oxide incorporated in the glass used to form the fibre, and the conditions of incorporation, are such that the glass contains from 1 to 50 parts per million by weight of ceric ions.

3. A method according to claim 1, wherein the total amount of cerium incorporated in the glass used to form the fibre is from 3 to 50 parts per million.

4. A method of forming an optical fibre according to claim 1, comprising the steps of melting a batch of glass-forming materials to form a phase-separable silicate glass and drawing or casting a rod of the glass; causing separation of silicate and non-silicate phases in the glass rod; leaching out the non-silicate phase to leave a porous rod; stuffing the porous rod with a dopant which increases the refractive index of the glass; dissolving the dopant out from an outer region of the porous rod; collapsing the porous rod by heating to produce a pre-form of a high silica glass with an inner region of higher refractive index; and drawing an optical fibre from the pre-form; wherein a cerium compound is introduced into the glass before the step of collapsing the porous rod, the operating conditions being such that in the pre-form and in the fibre a significant proportion of the cerium, amounting to 1 to 50 parts per million by weight of the glass, is in the form of ceric ions.

5. A method according to claim 4 wherein the cerium compound is introduced into the batch and the melting and the drawing or casting of the rod are carried out under oxidising conditions to ensure that a significant proportion of the cerium in the glass rod is in the form of ceric ions.

6. A method according to claim 5 wherein the cerium compound is introduced into the batch so that the phase-separable silicate glass contains from 0.1% to 1% by weight $CeO_2$.

7. A method according to claim 6 wherein the cerium compound is introduced into the batch so that the phase-separable silicate glass contains from 0.1% to 0.5% $CeO_2$.

8. A method according to claim 4 wherein the cerium compound is introduced with the dopant into the porous rod and the porous rod is collapsed under oxidising conditions to ensure that a significant proportion of the cerium is in the form of ceric ions.

9. A method according to claim 8 wherein the cerium compound is a cerous salt which is oxidised during the collapsing of the rod to produce the ceric ions.

10. A method according to claim 9 wherein the dopant is caesium nitrate and the cerium compound is cerous nitrate, both being applied to the porous rod in the same aqueous solution.

11. An optical glass fibre drawn from a glass containing at least 85 mol % silica and from 1 to 50 parts per million by weight of ceric ions, the attenuation characteristics of the fibre being such that the curve of attenuation plotted against wavelength shows no peaks due to drawing-induced colour centres and the attenuation in the wavelength range from 800 to 900 nm is not more than 20 dB/Km.

12. An optical glass fibre according to claim 11 wherein the total cerium in the fibre (cerous ions and ceric ions) is from 3 to 50 parts per million by weight of the glass.

* * * * *